(12) United States Patent
Manneschi (10) Patent No.: US 8,030,948 B2
(45) Date of Patent: Oct. 4, 2011

(54) DEVICE FOR ANALYZING THE COMPOSITION OF THE CONTENTS OF A CONTAINER COMPRISING MEANS FOR OBTAINING AT LEAST ONE ADDITIONAL PHYSICAL DATUM RELATING TO THE CONTAINER

(76) Inventor: Alessandro M. Manneschi, Arezzo (IT)

( * ) Notice: Subject to any disclaimer, the term of this patent is extended or adjusted under 35 U.S.C. 154(b) by 200 days.

(21) Appl. No.: 12/081,226

(22) Filed: Apr. 11, 2008

(65) Prior Publication Data

US 2008/0252302 A1  Oct. 16, 2008

(30) Foreign Application Priority Data

Apr. 12, 2007 (FR) ..................... 07 54440

(51) Int. Cl.
*G01R 27/32* (2006.01)
(52) U.S. Cl. ............... 324/639; 324/637; 324/640
(58) Field of Classification Search ............ 324/640, 324/639
See application file for complete search history.

(56) References Cited

U.S. PATENT DOCUMENTS

| 4,220,915 | A * | 9/1980 | Kawamoto et al. | 324/639 |
|---|---|---|---|---|
| 4,485,284 | A | 11/1984 | Pakulis | |
| 5,748,002 | A * | 5/1998 | Scott et al. | 324/633 |
| 7,239,150 | B2 * | 7/2007 | Troxler et al. | 324/643 |
| 7,394,262 | B2 * | 7/2008 | Manneschi | 324/639 |
| 7,442,935 | B2 * | 10/2008 | Manneschi | 250/339.12 |
| 2002/0050828 | A1 | 5/2002 | Seward, IV et al. | |
| 2008/0252305 | A1 * | 10/2008 | Manneschi | 324/693 |
| 2009/0146061 | A1 * | 6/2009 | Manneschi | 250/339.12 |
| 2009/0206285 | A1 * | 8/2009 | Manneschi | 250/573 |

FOREIGN PATENT DOCUMENTS

| CA | 2543196 | A1 * | 10/2006 |
|---|---|---|---|
| EP | 1 712 900 | A1 | 10/2006 |
| EP | 1712899 | A2 * | 10/2006 |
| FR | 2 884 612 | A1 | 10/2006 |
| FR | 2 884 613 | A1 | 10/2006 |
| FR | 2884612 | A1 * | 10/2006 |
| GB | 1 392 708 | | 4/1975 |
| WO | WO 00/14552 | A1 | 3/2000 |

OTHER PUBLICATIONS

Klock et al., "Usability Assessment of a Bottle Content Tester for Use in Airports by Screeners," Security Technology, 2000, Proceedings IEEE 34th Annual 2000 International Carnahan Conference, Oct. 23-25, 2000, Oct. 23, 2000, 174-177.

* cited by examiner

*Primary Examiner* — Thomas Valone
(74) *Attorney, Agent, or Firm* — Foley & Lardner LLP

(57) ABSTRACT

A device for analyzing the contents of a container includes electromagnetic field emitting/receiving means (40) at least several frequencies in a determined range of frequencies, means (22) supporting a container (R), the contents of which have to be analyzed, suitable for ensuring accurate relative positioning between the emitting/receiving means (40) and the container (R), means (50) capable of measuring the complex impedance of the emitting/receiving means influenced by the load formed by the container (R) and its contents, representative of the complex dielectric characteristics of the container and of its contents, means (53, 55) for obtaining at least one additional physical datum relating to a characteristic of the container (R), and means (50) capable of providing information relating to the nature of the contents of said container (R) depending on the measured complex impedance and on the additional physical datum.

13 Claims, 5 Drawing Sheets

DEVICE FOR ANALYZING THE COMPOSITION OF THE CONTENTS OF A CONTAINER COMPRISING MEANS FOR OBTAINING AT LEAST ONE ADDITIONAL PHYSICAL DATUM RELATING TO THE CONTAINER

The present invention relates to the field of analyzing the composition of the contents on containers such as bottles.

The present invention may find many applications. It may notably be applied to production control in bottling factories in order to avoid any tampering on the contents of containers subsequently provided to the general public. The invention may also be applied to the checking of luggage transported by passengers, in particular hand luggage kept by passengers in airports.

STATE OF THE ART

The well-known X-ray examination means do not allow the contents of bottles or equivalent containers to be determined. Such examination means actually only allow classification into two categories, organic materials and non-organic materials. They do not allow a distinction to be made between two organic materials.

In order to overcome this drawback, a device for analyzing the composition of the contents of a container was developed.

This device comprises means for emitting/receiving an electromagnetic field at least several frequencies comprised in a determined range of frequencies, means for supporting a container, the contents of which has to be analyzed, suitable for providing an accurate relative positioning between the emitting/receiving means and the container, means capable of measuring the complex impedance of emitting/receiving means influenced by the load formed by the container and its contents, representative of the complex dielectric characteristics of the container and its content, and means able to provide information related to the measured complex impedance and therefore to the nature of the contents of said container.

An advantage of this device is that it allows the contents of a container to be detected with great reliability.

An object of the invention is to propose a device with which the reliability of the aforementioned device may be improved.

SUMMARY OF THE INVENTION

For this purpose, a device for analyzing the composition of the contents of a container is proposed, comprising:
- means for emitting/receiving an electromagnetic field at, at least several frequencies comprised in a determined range of frequencies,
- means for supporting a container, the contents of which have to be analyzed, suitable for providing accurate relative positioning between the emitting/receiving means and the container,
- means capable of measuring the complex impedance of the emitting/receiving means, influenced by the load formed by the container and its contents, representative of the complex dielectric characteristics of the container and of its contents,
- means for obtaining at least one additional physical datum relating to a characteristic of the container, and
- means capable of providing information relating to the nature of the contents of said container depending on the measured complex impedance and on the additional physical datum.

Preferred but non-limiting aspects of the device according to the invention are the following:
- the additional physical datum comprises the mass of the container and of its contents;
- the means for obtaining at least one additional physical datum comprise a gravimetric sensor for measuring the mass of the container and of its contents;
- the gravimetric sensor is positioned under the means for supporting the container;
- the tare of the device is periodically measured by the gravimetric sensor when no container is introduced into the support;
- the presence of a container on the support is detected by the means capable of measuring the complex impedance of the emitting/receiving means;
- the means capable of providing information are capable of providing information relating to the nature of the contents of said container depending on the measured complex impedance and on the measured mass;
- the means capable of providing information comprise means capable of correcting the amplitude of the measured complex impedance depending on the measured mass, of comparing the corrected complex impedance with reference values predetermined for the same range of frequencies, and of generating an alarm when the measured complex impedance deviates from the reference values;
- the additional physical datum comprises the capacity of the container and/or the material making up the walls of the container and/or the thickness of the walls of the container;
- the additional physical datum comprises the material making up the walls of the container, the material being selectable from glass or plastic;
- the means for obtaining at least one additional physical datum comprise input means for inputting the additional physical datum;
- the means are capable of providing information relating to the nature of the contents of the container depending on the measured complex impedance and on the additional physical datum inputted by a user on input means;
- the means capable of providing information (or means of analysis) comprise means capable of comparing the measured complex impedance with reference values predetermined for the same range of frequencies, the means ordering the user to input the additional physical datum on the input means, when the measured complex impedance deviates from the reference values;
- inputting the additional physical datum by means of the input means by selecting characteristics of containers from a predetermined list of characteristics of containers.

PRESENTATION OF THE FIGURES

Other characteristics, objects and advantages of the present invention will become apparent upon reading the detailed description which follows, and with reference to the appended drawings, given as non-limiting examples and wherein:

FIGS. 10a, 10b and 10c illustrate a fifth alternative embodiment, whereas

DESCRIPTION OF THE INVENTION

The present invention is essentially based on the following approach.

Dielectric materials have four basis polarizations: electronic, ionic, dipole, and migrational polarizations.

Each type of polarization is characterized by a assemblyting-up time, called a rise time. If the excitatory electromagnetic field has an angular frequency larger than the reciprocal of the rise time, polarization cannot be achieved. Consequently, polarization is present only at frequencies below the cut-off frequencies and absent at higher frequencies. In the transition zone, a phenomenon occurs with a loss of energy in the dielectric due to the rotation of molecules out of phase with respect to the excitatory field.

The rise times for electronic polarization are from $10^{-14}$ to $10^{-15}$ seconds, i.e. in the optical domain. Such a range of frequencies is difficult to utilize on an industrial scale because the bottles to be examined may frequently be partly or completely opaque.

Ionic polarization has rise times comprised between $10^{-13}$ and $10^{-14}$ seconds, very close to electronic relaxation times. It is also therefore difficult to utilize.

Dipole polarization is characteristic of polar dielectrics (as water for example).

Dipole polarizations, unlike electronic and ionic polarizations, which are inertialess, persist for a certain time after extinction of an excitation. Dipole polarization decreases with an exponential low and a time constant, called the relaxation time, comprised between $10^{-6}$ and $10^{-11}$ seconds, i.e. in the radiofrequency domain. Electromagnetic waves having these frequencies may pass through glass, plastic and other dielectric materials. The applicant thus determined that electromagnetic waves may be used for examining the contents of bottles or equivalent containers.

Migrational polarization is present in certain dielectrics, in particular in heterogeneous materials, which contain impurities. In this case, the charges move very slowly and the rise time may be of several seconds, minutes, or even sometimes hours. This type of polarization is therefore only measurable at a very low frequency.

Figure 3:
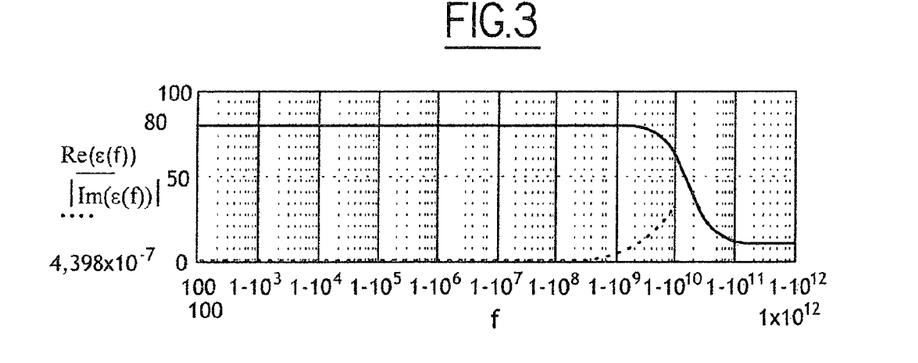
FIG. 3 illustrates the real part and imaginary part of the measured complex impedance in the case of a load consisting of water, over a wide range of frequencies.

Water which is a polar liquid, and therefore water-based liquids, have a relaxation time of the order of $10^{-11}$ seconds at room temperature, corresponding to a frequency of about 16 GHz. The measurement of the complex dielectric constant at a lower frequency than the relaxation frequency show a high real part and limited losses (distilled water) as illustrated by the appended FIG. 3.

Saturated hydrocarbons $C_nH_{2n+2}$ are non-polar molecules or with a very low electric dipole moment, therefore they do not exhibit a dipole polarization phenomenon and the value of the real part of the dielectric constant is low (relative dielectric constant of the order of 2). Losses in hydrocarbons are negligible right up to very high frequencies. If a hydrocarbon molecule loses its symmetry such as for example in the case of ethyl or methyl alcohol, an electric dipole moment appears and therefore a constant larger than the one obtained in the case of hydrocarbons, and a resonance phenomenon occurs at the dipolar relaxation frequency.

The physical phenomena described above have been known since the end of the 30ies (see Peter Debye Nobel Lecture, 1936, for example).

However, they have not up to now been applied for efficient analysis of the contents of containers.

Figure 1:
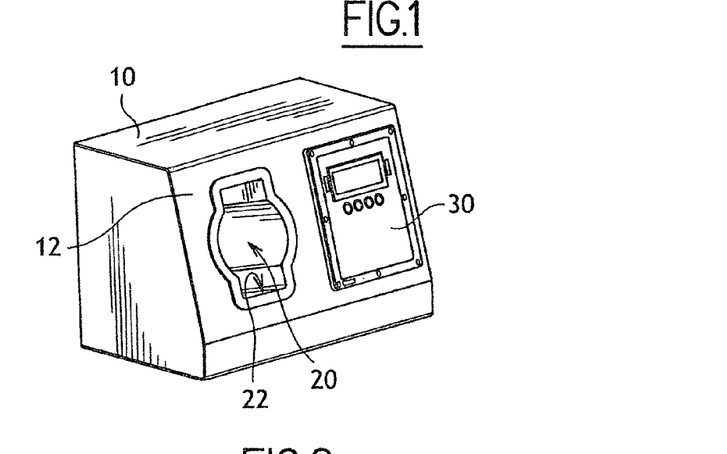
FIG. 1 illustrates a schematic perspective view of an analysis device according to a first embodiment of the present invention.

The casing of an analyzing device according to the present invention is illustrated in FIG. 1.

The general geometry of this casing may be the subject of many alternative embodiments and will therefore not be described in detail subsequently.

Preferably, this casing comprises a metal case 10 in order to form a shield around the electromagnetic sensor according to the invention with respect to the external environment.

Preferably, this case defines a cavity 20, the lower portion of which 22 has concavity directed upwards, designed for receiving a container to be analyzed and for guaranteeing accurate positioning of the latter relatively to the electromagnetic field emitting/receiving means according to the invention.

Still more specifically, preferably, within the scope of the present invention, the aforementioned cavity 20 is formed by a channel with constant cross-section, the generatrices of which are tilted downwards away from the open front face 12 through which a container is introduced.

The rear face of this cavity or channel 20 is preferably closed in order to prevent the analyzed container from sliding on the bottom 22.

The cross-section of the channel 20 may be the object of many alternatives. A first alternative is illustrated in FIG. 1, according to which the channel 20 has a cross-section with a keyhole shape comprising a cylindrical central portion extended with two diametrically opposite protrusions of an overall rectangular contour. The advantages of the different alternative cross-sections will be explained in the following.

Figure 4:
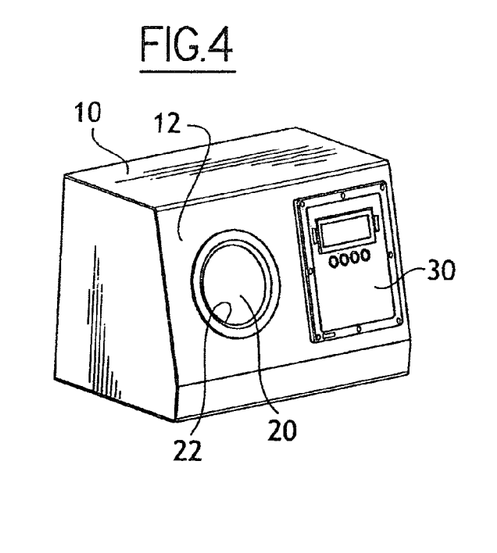
FIGS. 4 and 5 illustrate two schematic perspective views of alternatives of the device illustrated in FIG. 1, FIGS. 6, 7, 8 and 9 illustrate four alternative embodiments of emitting/receiving electromagnetic sensors according to the present invention.

An alternative embodiment is illustrated in FIG. 4, according to which the channel 20 has a circular cross-section. Another alternative embodiment is illustrated in the appended FIG. 5, according to which the channel 20 has a square or even rectangular cross-section, the diagonals of which are respectively vertical and horizontal so that an edge coincides with the lowest point of the channel 20.

Figure 5:
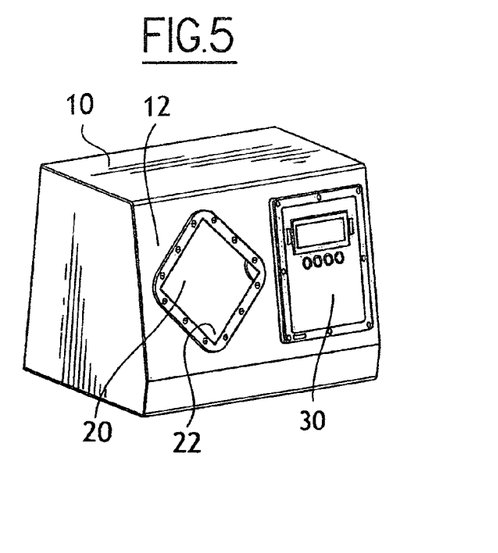

As this is seen in the appended FIGS. 1, 4 and 5, the casing 10 further preferably includes a control console 30 equipped with an input keyboard and/or programming keyboard, a display device and network presence and alarm signalling (light and/or sound) means. In this respect, the invention of course is not limited to the particular embodiments illustrated in the appended figures.

Preferably, the cavity 20 is coated with a plastic protective coating.

Figure 2:
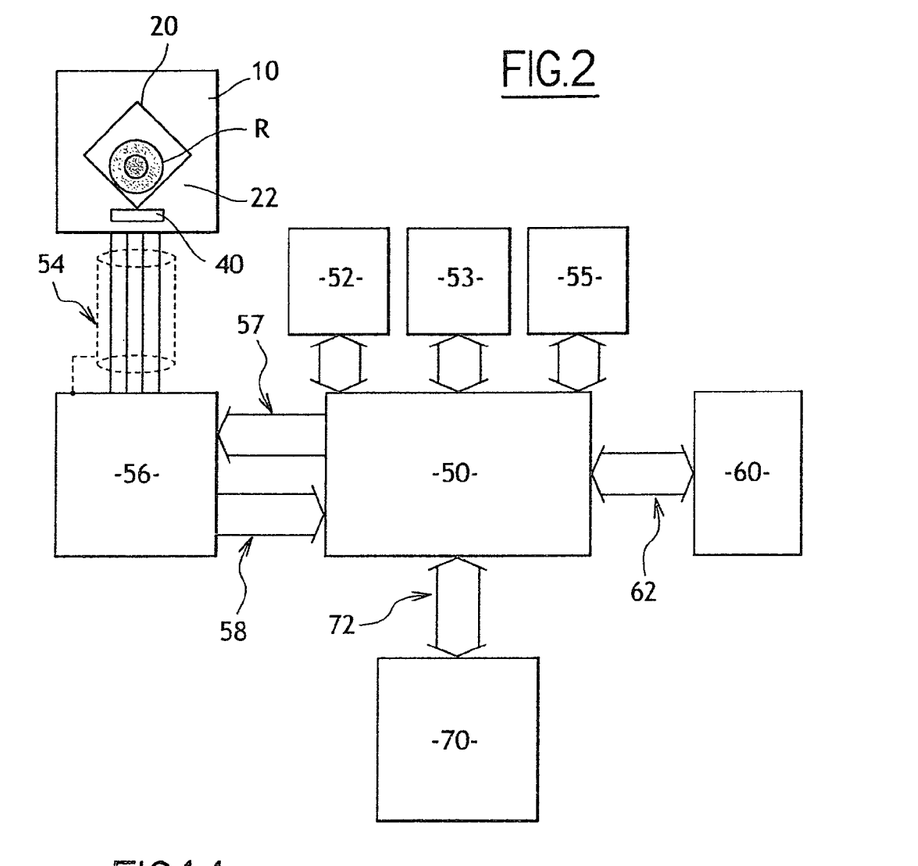
FIG. 2 illustrates a schematic view as functional blocks of the essential elements making up this device.

As this is illustrated in FIG. 2 in which a container to be analyzed is schematized under reference R and in which the bottom 22 of the cavity 20 is again found, preferably the electromagnetic sensor(s) intended for measuring the complex dielectric characteristics of the bottom R and of its contents is(are) placed around the cavity 20.

These electromagnetic field emitting/receiving means are preferably formed with one or more transducers (antennas) 40 connected via a connection network 54, an electromagnetic measurement network 56 and buses 57, 58 to a generator 50, designed for emitting an electromagnetic wave. Typically, the generator 50 is adapted so as to cover the range of frequencies ranging from a few Hz, for example 5 Hz to a few GHz, for example 20 or 50 GHz. The generator 50 is applied either manually by an operator when the latter introduces a container R into the channel 20, or automatically under the effect of a sensor 52 designed for detecting the presence of a container R in the channel 20.

The means 50 are moreover designed for measuring the complex impedance of the emitting means 40, influenced by the load formed by the container R and its contents, representative of the complex dielectric characteristics of this container R and of its contents. More specifically, the means 50 are designed in order to measure this complex impedance at several frequencies sampled over the aforementioned excitation range from a few Hz to several GHz. Typically, the means 50 thus operate over a number of frequencies comprised between 10 and 50, advantageously over about thirty frequencies.

Moreover, the means 50 are suitable for providing information related to the measured complex impedance and to the nature of the contents of the accordingly detected container.

Preferably, these means 50 are suitable for comparing the thereby measured complex impedance with reference values predetermined for the same range of frequencies and generating an alarm when the measured complex impedance deviates from the reference values.

A memory 60 coupled with analysis means 50 via a communication bus 62 is illustrated in FIG. 2, and in which reference values predetermined over the working frequency range may be stored in memory. Moreover in the same FIG. 2, alarm means are illustrated under reference 70, preferably present on the control console 30, connected to means 50 via a communications bus 72 and suitable for generating a sound and/or visual alarm, when the measured complex impedance deviates from the reference values.

Alternatively, the reference values may be computed by the means 50 and not be contained in a memory 60.

Moreover, according to another alternative, the means 70 may be suitable for directly indicating the nature of the contents of the container R or at least the family of these contents instead of or as a complementary addition to the aforementioned alarm means.

The electromagnetic field emitting/receiving means 40 may be the object of many embodiments.

Figure 6:
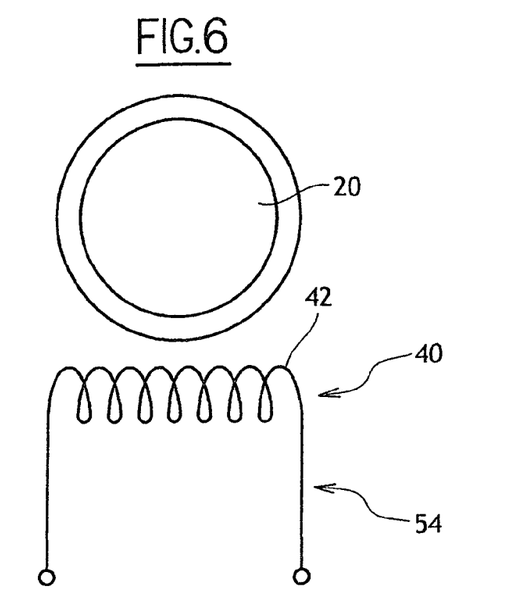

FIG. 6 illustrates a first embodiment in which these means 40 are formed with a simple winding 42 forming the emitter and receiver, connected via a two-wire network 54 to the means 56.

Figure 7:
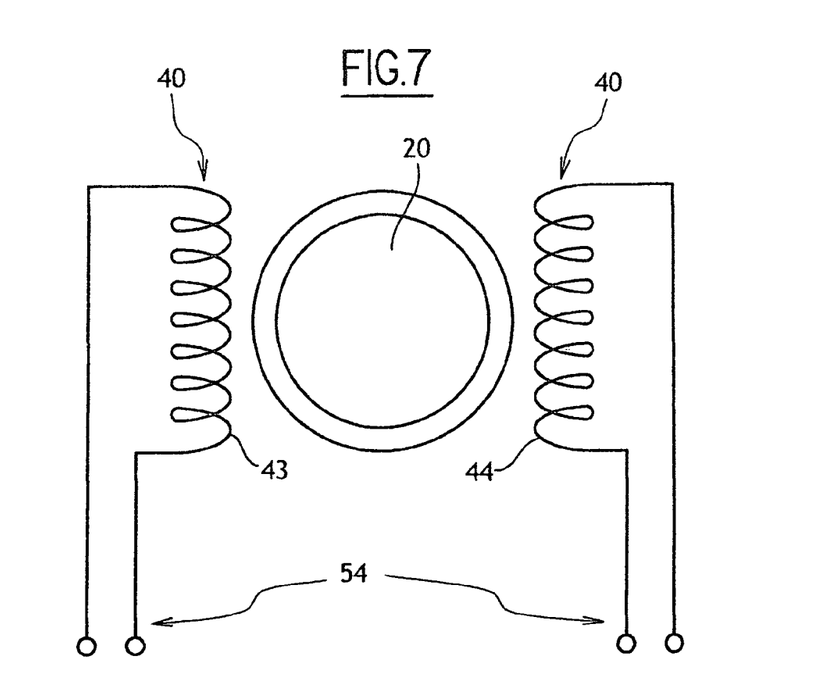

FIG. 7 illustrates a second embodiment wherein the means 40 are formed with two windings 43, 44 respectively, and if necessary alternatively, forming an emitter and receiver connected via a four-wire network 54 to the means 56.

Figure 8:
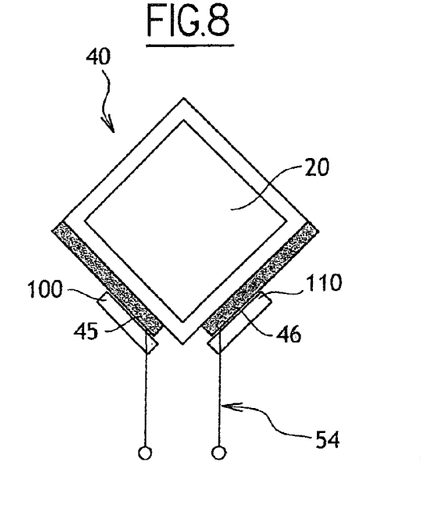

FIG. 8 illustrates a third embodiment wherein the means 40 are formed with two frames 45, 46 of a capacitance surrounding the cavity 20 intended to receive the container R and connected via a two-wire network 54 to the means 56.

Figure 9:
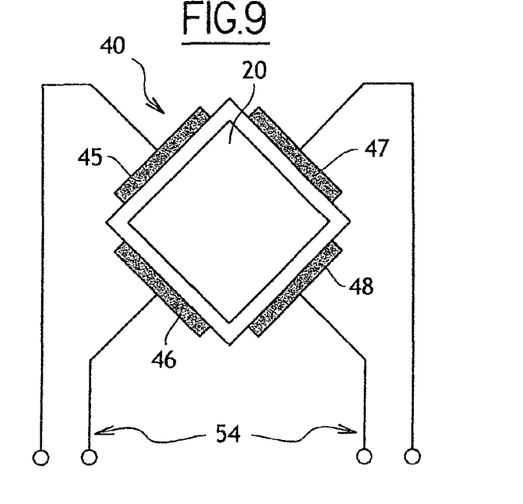

FIG. 9 illustrates an alternative of FIG. 8 wherein the means 40 comprise (two) six crossed capacitances consisting of four frames 45, 46, 47, 48 connected via a four wire network 54 to the means 56 and respectively, and if necessary alternatively, forming an emitter and receiver.

Figure 10A:
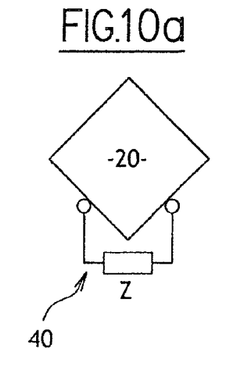
Figure 10B:
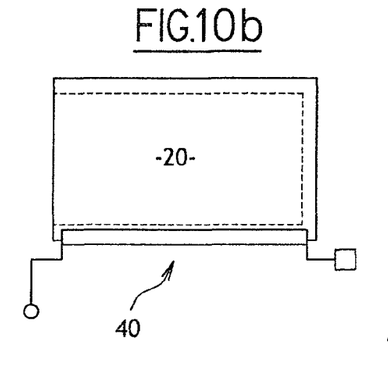
Figure 10C:
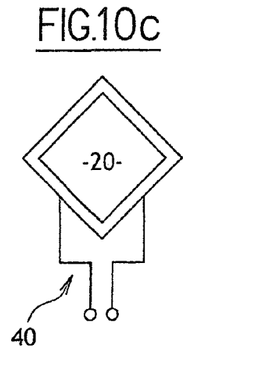

FIGS. 10a, 10b, 10c illustrate another alternative embodiment according to which the means 40 are formed with transmission lines. Typically, these transmission lines operate in the microwave domain. They may be formed with two-wire lines or wave guide with slots.

Figure 11A:
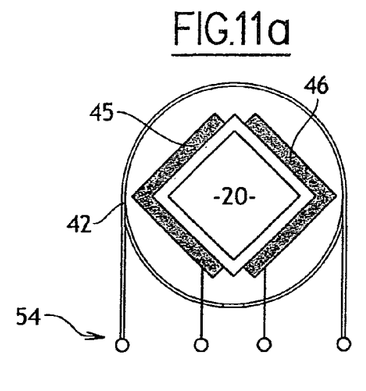
FIGS. 11a and 11b illustrate a sixth alternative embodiment of emitting/receiving electromagnetic sensors according to the present invention.
Figure 11B:
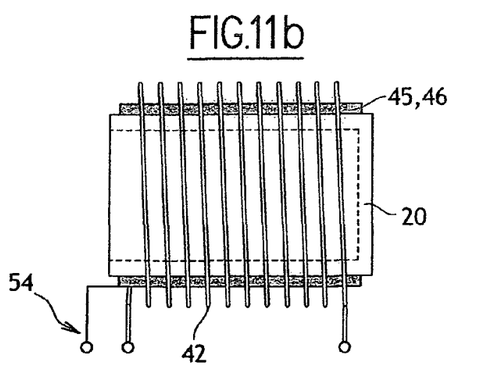

Moreover, within the scope of the present invention, as illustrated in FIGS. 11a and 11b, sensors may be used which simultaneously apply an inductive transducer 42 and a capacitive transducer 45, 46. With this arrangement it is possible to detect that the increase in the real part of the complex dielectric constant is due to an internal metal frame of the container and not to one or more liquids having particular properties.

With this arrangement, it is thus possible to detect the presence of metal screens capable of forming a shield perturbing the measurement. The inductive sensor 42 powered by an alternating current source in this case will produce eddy currents in the metal portion. These currents will be measured by the processing device. And comparing the signals from the electric field transducers 45, 46 and from the magnetic field transducer 42 allows satisfactory detection.

Of course, the number of means making up the emitters and/or receivers is by no means limited and may be larger than those illustrated in the appended figures.

One skilled in the art will understand upon reading the detailed preceding description that the present invention thus proposes an electromagnetic sensor with a high frequency sweep, with which the dielectric characteristics of the bottle R and of its contents may be measured.

Once the object R to be analyzed is positioned in the cavity 20, the generator 50 is activated, either manually or automatically, and the complex impedance of the network formed by the emission/reception circuit 40 influenced by the container R and its contents is measured.

The measured impedance depends on the transmission/reception circuit and on the load, represented by the examined bottle. This complex impedance consists of a real part related to losses (conductibility) in the analyzed object R and of an imaginary part, related to the dielectric characteristics.

Measurement of the impedance is carried out at different frequencies in the determined range.

All drinkable water-based liquids, such as non-alcoholic beverages, wine and liquors are well identifiable by their polar dielectric characteristics, with a high dielectric constant and losses located between a minimum and a predetermined value. A value different from the typical one of drinkable liquids will therefore be detected and will cause an acoustic and/or visual alarm, plus if necessary, possible messages on the display device or even according to the retained alternative, directly the indication of the nature of the detected contents.

As described earlier, the cross-section of the channel 20 may be the object of many alternatives. For example, the cross-section may be in the shape of a keyhole as illustrated in FIG. 1, the cross-section may also be of a circular shape as illustrated in FIG. 4 or of a square or even rectangular shape (with vertical and horizontal diagonals) as illustrated in FIG. 5.

For certain geometries of the cross-section of the channel, the measured complex impedance may vary depending on the volume of the container in which a same analyzed liquid is contained.

Figure 12A:
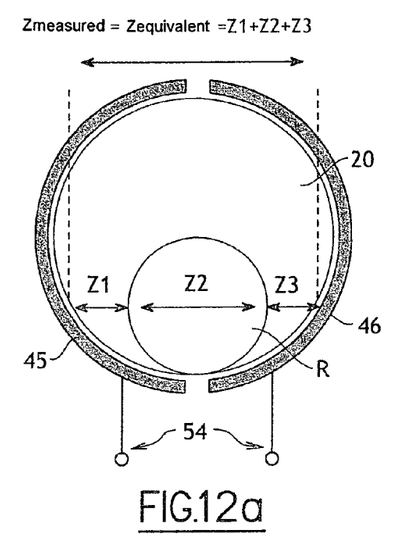
FIGS. 12a and 12b, and 13a and 13b illustrate alternative embodiments of the invention used for analyzing containers with variable volumes.
Figure 12B:
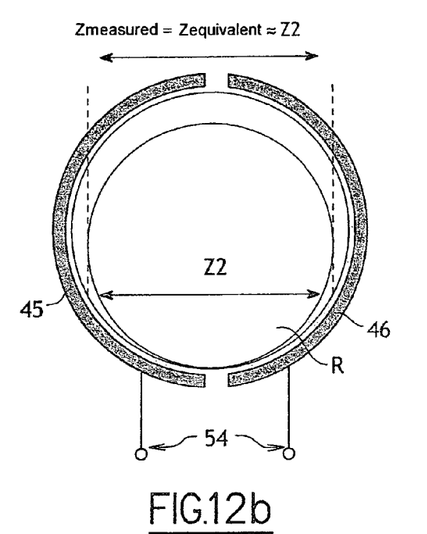

Thus, in the case of a channel 20, the cross-section of which is of a circular shape as illustrated in FIGS. 12a and 12b, the measured complex impedance $Z_{measured}$ for a 50 centiliter container R containing water (FIG. 12a) will be different from the measured complex impedance $Z_{measured}$ for a 2 liter container R containing water (FIG. 12b).

This is due to the fact that the measured complex impedance $Z_{measured}$ corresponds to the equivalent complex impedance $Z_{equivalent}$ of the whole of the dipoles located between the frames 45, 46 of the electromagnetic field emitting/receiving means.

In FIGS. 12a and 12b, a device is illustrated comprising a channel 20 with a cross-section of circular shape, specially adapted for measuring the complex impedance of the contents of a cylindrical 2 liter bottle, i.e. a channel 20, the diameter of the cross-section of which is slightly larger than the diameter of a 2 liter cylindrical bottle.

As illustrated in FIG. 12a, when this device is used with a container R of 50 centiliters, positioned in the channel 20 so that its longitudinal axis of the container R is substantially horizontal, the measured complex impedance $Z_{measured}$ is equal to the sum of the complex impedance of the water $Z_2$ contained in the container R and of the complex impedances $Z_1$ and $Z_3$ of the air located between the walls of the container R and the frames 45, 46.

The complex impedances $Z_1$ and $Z_3$ of the air located between the walls of the container R and the frames 45, 46 are considered to be parasitic impedances which should be minimized so that the measured complex impedance is substantially equal to the complex impedance of the liquid contained in the container to be analyzed.

As illustrated in FIG. 12b, when this device is used with a 2 liter container for which the cross-section is specially adapted, the measured complex impedance $Z_{measured}$ is substantially equal to the complex impedance of the water $Z_2$ contained in the container R.

Indeed, with a 2 liter container for which the cross-section is specially adapted, the parasitic impedances $Z_1$ and $Z_3$ become negligible because the distances between the walls of the container R and the frames 45, 46 are small.

The square (or rectangular) and keyhole geometries of the cross-section have the advantage of making the measurement of the complex impedance independent of the volume of the container in which the liquid to be analyzed is contained.

Indeed, with these geometries it is possible to limit the distance between the walls of the container R and the frames 45, 46 of the electromagnetic field emitting/receiving means regardless of the volume of the container R.

Figure 13A:
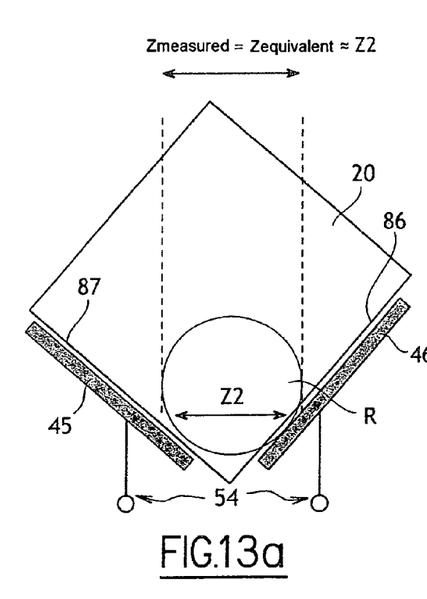
Figure 13B:
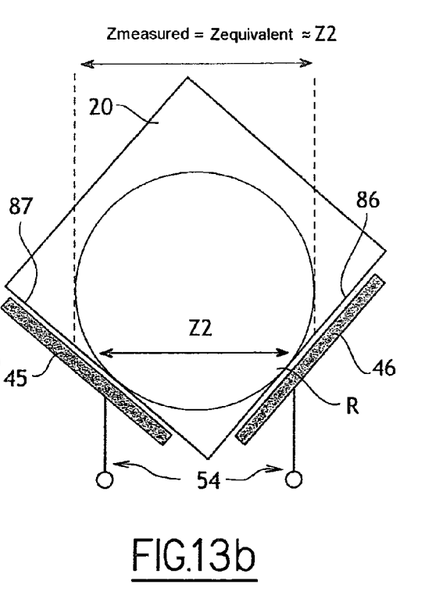

In FIGS. 13a, 13b a device according to the present invention is illustrated, comprising a channel 20 with a square-shaped cross-section, the diagonals of which are respectively vertical and horizontal so that an edge coincides with the lowest point of the channel 20.

In the case of a container R of a cylindrical shape placed in the channel 20 so that the longitudinal axis of the container R is horizontal, the container R will tend to come into contact with the partitions 86, 87 of the channel 20 because of gravity, as illustrated in FIGS. 13a and 13b.

Thus, the distance between the walls of the container and the frames 45, 46 (which are very close to the partitions 86, 87 of the channel 20) is quasi zero regardless of the diameter of the container containing the liquid to be analyzed, so that the parasitic impedances $Z_1$ and $Z_3$ of the air located between the walls of the container R and the frames are negligible. The measured impedance $Z_{measured}$ is substantially equal to the complex impedance of the liquid contained in the container R regardless of the volume of the container R used.

Just as for a channel, for which the cross-section is square, with a keyhole-shaped cross-section geometry, it is possible to minimize the distance between the walls of the container containing the liquid to be analyzed and the frames of the device regardless of the volume of the container R used, so that the measurement of the complex impedance is independent of the volume of the container in which the liquid to be analyzed is contained. Thus, in the case of a 50 cl cylindrical container, the latter is positioned between the lower protrusion of the keyhole-shaped cross-section (the distance between these protrusions may be provided to be slightly larger than the diameter of a 50 centiliter cylindrical bottle of a standard type). In the case of a 2 liter container, the latter is positioned at the cylindrical central portion of the keyhole-shaped channel.

Thus, the channel 20 of the device preferentially defines a concavity 22 directed upwards. Even more preferentially, the convergence of the partitions 86, 87 of the channel 20 is determined so that not only the distance between the lowest point of the channel 20 and the centre of gravity of the container R increases as a function of the volume of the container R but the point of contact of the container R on the walls of the channel 20 further increases and the height of the base of the container relatively to the lowest point of the channel 20 also increases as a function of the volume of the container R. Still more preferentially, the concavity 22 directed upwards is obtained by means of two rectilinear sections so as to minimize the effect of the parasitic impedances $Z_1$ and $Z_3$ of the air located between the walls of the container R and the partitions 86, 87 of the channel 20.

With the device described earlier, it is possible to have non-destructive investigation means for determining the composition of the contents of a container.

In order to increase the reliability of the analysis device, it is proposed to integrate to this device means 53, 55 with which an additional physical datum relating to a characteristic of the analyzed container may be obtained.

In an alternative of the invention, the means with which an addition physical datum may be obtained comprise means for measuring the mass of the analyzed container R.

Indeed, when the capacity of the analyzed container is small (i.e. less than 200 mL), the device described earlier tends to underestimate the complex impedance of the liquid contained in the analyzed container, which may lead to the emission of a false alarm.

More specifically, the complex impedance per unit volume of a liquid measured in a container with for example a capacity of 100 mL will be less than the complex impedance per unit volume of the same liquid measured in a 2 L container.

The same applies when a square-shaped container is placed in a channel with a square cross-section. More specifically, the measured complex impedance of a liquid contained in a 1 L container with a square cross-section will be larger than the measured complex impedance of the same liquid contained in a cylindrical container.

This is so because in both cases, the walls of the container (of square cross-section or of small capacity) cooperate differently with the walls of the channel.

It is therefore proposed in order to increase the reliability of the device described earlier to provide the analysis means 50 with an additional datum in addition to the measured complex impedance.

This additional datum is the mass of the container and preferentially of the container with its contents.

In order to measure the mass of the container and of the liquid which it contains, the device comprises a gravimetric sensor 53.

Preferentially, the gravimetric sensor 53 is positioned integrated to the channel 20.

More specifically, the gravimetric sensor is positioned under the lower portion (or bottom 22) of the channel 20. This allows the bulkiness of the device to be limited.

The device then operates as follows.

The tare of the device is periodically measured. More specifically, when no container is introduced into the channel 20, the gravimetric sensor 53 measures the mass of the lower portion 22 of the channel 20. This measured tare is sent to the means 50.

The presence of a container in the channel 20 is detected:
either by the sensor 52,
or by the means 50.

In the case when the presence of a container is detected by the means 50, this detection is carried out as follows. The user introduces a container on the lower portion 22 of the channel 20. The complex impedance of the emitting/receiving means is influenced by the load formed by the container R and its contents. The analysis means 50 detect this change in complex impedance and emit a signal indicating the presence of a container to be analyzed in order to interrupt the periodical updating of the tare of the device.

The gravimetric sensor 53 measures the mass of the container R and of its contents and sends a signal representative of the measured mass to the analysis means 50.

The analysis means 50 associate the measured mass with the measured complex impedance for the analyzed container R.

More specifically, the measured mass is used for correcting the amplitude of the measured complex impedance.

The thereby corrected complex impedance is then compared with reference values for determining the nature of the liquid contained in the container R.

Figure 14:
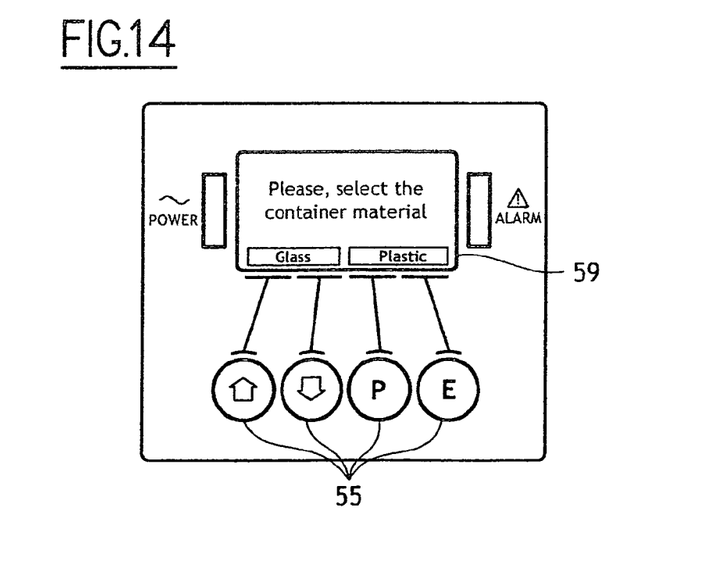
FIG. 14 illustrates an embodiment of viewing and input means of the device.

In another alternative of the invention, the means with which an addition physical datum may be obtained comprise input means 55 illustrated in FIGS. 2 and 14.

The input means 55 may allow the input of additional data relating to the analyzed container.

By means of these additional data, the selectivity of the device may be increased.

Indeed, by knowing additional data, it is possible to reduce the acceptance window on the measured complex impedance. Without any additional data, the acceptance window should be sufficiently wide in order to take into account the variability of physical factors relating to different types of container which may be analyzed such as:
the material forming the walls of the container,
the thickness of the walls of the container,
the capacity (or volume) of the container.

The device may therefore comprise input means 55 for inputting additional data relating to the analyzed container.

In order to facilitate the use of the device, the analysis means 50 propose questions displayed on the display means 59 as well as a list of possible answers.

With the help of the input means 55, the user selects, depending on the analyzed container, the most appropriate answer from the list of proposed answers.

The additional data which the user should input may be the capacity (i.e. the volume) of the container and/or the material making up the walls of the container and/or the thickness of the walls of the container.

Advantageously, the analysis means 50 display questions relating to the analyzed container exclusively when the input of additional data relating to the analyzed container is required for determining the nature of the liquid contained in the analyzed container.

In this case, the means (50) provide information relating to the nature of the contents of the container depending on the measured complex impedance and on the datum(a) inputted by the user on the input means 55.

For example, when the measured complex impedance deviates from the reference values, the analysis means 50 order the user (via the display means 59) to input additional data on the input means 55.

In still another alternative, the means with which an additional physical datum may be obtained comprise means for measuring the mass on the one hand and input means on the other hand.

Of course, the present invention is not limited to the particular embodiments which have just been described but extend to any alternative in accordance with its spirit.

It will moreover be noted that within the scope of the present invention, the sensors 40 are preferably suitable for covering at least a substantial portion of the containers, or even the totality of the latter. This guarantees a high security level in the analysis, since this allows the entirety of the contents of the containers to be analyzed and not only a portion of the latter.

When a single transducer is provided, the latter is an emitter and receiver simultaneously or successively.

When several transducers are provided, all the combinations are possible, i.e. these transducers may simultaneously or successively be an emitter and/or a receiver.

According to another advantageous characteristic, the analysis device according to the present invention further comprises an ionizing or radioactive radiation detector assembly. This assembly is intended to detect the possible presence of traces of radioactive products in the analyzed container.

The ionizing or radioactive radiation detector assembly may be the object of many embodiments. It may be formed with any structures known to one skilled in the art, in particular any structure capable of converting a detected ionizing ray into a utilizable electric signal. For example and in a non-limiting way, this may be a Geiger type detector comprising a tube or a chamber which houses a gas, the composition of which is selected in order to generate a ionizing discharge during the detection of active radiation, and from there an electric pulse. This may also be a scintillator detector capable of converting the detected energy into light scintillations then converted into an electric signal by a network of photomultipliers. Many scintillators have been proposed for this purpose, for example based on sodium iodide, caesium iodide or even bismuth germanate.

The ionizing radiation detector 7 is placed in any suitable location and preferably in close proximity to the walls of the cavity 20, on the outside of the latter. In FIG. 8 under reference 100, 110, an a priori optimum localization of this assembly is illustrated, under the cavity 20 against both walls forming the lower dihedron of the cavity 20.

The ionizing radiation detector assembly 100, 110 is suitable for operating in masked time, in parallel with the device for measuring complex impedance described earlier. The ionizing radiation detector assembly 100, 110 is controlled and put into service by any suitable means detecting the presence of a container in the cavity. Preferably, but in a non-limiting way, the ionizing radiation detector assembly is thus initiated by a signal sampled on the chain from measuring complex impedance and representative of the presence of such a container in the channel 20.

Several embodiments of means 40 forming electromagnetic fields emitters/receivers have been described earlier. Within the scope of the present invention, means are preferably provided with which the configuration of the emitter-forming means and of the receiver-forming means may be changed, in order to enrich the available information, for example on the volume of the analyzed container.

In particular, an alternative embodiment is illustrated in FIG. 9 according to which the means 40 comprise four capacitive frames 45, 46, 47 and 48 respectively positioned on the outside of each of the four faces of a square cross-section of the channel 20. In this context, switching means are preferably provided within the measurement network 56, for changing the configuration of the means 40 so that in a first configuration, one of both lower frames 46 or 48 forms an emitter whereas the other lower frame 48 or 46 forms a receiver, and a second configuration wherein both lower frames 46 and 48 form emitters whereas both upper frames 45 and 47 form receivers or vice versa.

The invention claimed is:

1. A device for analyzing the composition of the contents of a container comprising:

electromagnetic field emitting/receiving means at least several frequencies comprising a determined range of frequencies, means for supporting the container, the contents of which have to be analyzed, suitable for ensuring accurate relative positioning between the emitting/receiving means and the container, means for measuring the complex impedance of the emitting/receiving means influenced by the load formed by the container and its contents, representative of the complex dielectric characteristics of the container and its contents, means for obtaining at least one additional physical datum relating to a characteristic of the container, the additional physical datum comprising the mass of the container and its contents, and means for providing information relating to the nature of the contents of said container depending on the measured complex impedance and on the mass of the container and its contents, the mass of the container and its contents being used for correcting the amplitude of the measured complex impedance.

2. The device of claim 1, wherein the means for obtaining at least one additional physical datum comprise a gravimetric sensor for measuring the mass of the container and of its contents.

3. The device of claim 2, wherein the gravimetric sensor is positioned under the means for supporting the container.

4. The device of claim 2, wherein a tare of the device is periodically measured by the gravimetric sensor when no container is introduced into the support.

5. The device of claim 1, wherein the presence of a container on the support is detected by the means for measuring the complex impedance of the emitting/receiving means.

6. The device of claim 1, wherein the means for providing information are capable of providing information relating to the nature of the contents of said container depending on the measured complex impedance and on the measured mass.

7. The device of claim 1, wherein the means for providing information comprise means capable of correcting the amplitude of the measured complex impedance depending on the measured mass, of comparing the corrected complex impedance with reference values predetermined for the same range of frequencies, and of generating an alarm when the measured complex impedance deviates from the reference values.

8. The device of claim 1, wherein the at least one additional physical datum comprises the capacity of the container and the material making up the walls of the container and the thickness of the walls of the container.

9. The device of claim 1, wherein the additional physical datum comprises the material making up the walls of the container, wherein the material comprises glass or plastic.

10. The device of claim 1, wherein the means for obtaining at least one additional physical datum comprise input means for inputting the additional physical datum.

11. The device of claim 10, wherein the means for providing information are capable of providing information relating to the nature of the contents of the container depending on the measured complex impedance and on the additional physical datum inputted by a user on the input means.

12. The device of claim 10, wherein the means for providing information comprise means for comparing the measured complex impedance with reference values predetermined for the same range of frequencies, the means for providing information ordering the user to input the at least one additional physical datum on the input means, when the measured complex impedance deviates from the reference values.

13. The device of claim 10, wherein the additional physical datum is inputted with the help of input means by selecting characteristics of containers from a predetermined list of characteristics of containers.

* * * * *